(12) United States Patent
Wübbeling et al.

(10) Patent No.: US 11,576,799 B2
(45) Date of Patent: Feb. 14, 2023

(54) DELIVERY SYSTEM FOR A PROSTHESIS

(71) Applicant: C. R. Bard, Inc., Murray Hill, NJ (US)

(72) Inventors: Martin Wübbeling, Mannheim (DE); Jutta Mair, Ettlingen (DE)

(73) Assignee: C. R. Bard, Inc., Franklin Lakes, NJ (US)

( * ) Notice: Subject to any disclaimer, the term of this patent is extended or adjusted under 35 U.S.C. 154(b) by 479 days.

(21) Appl. No.: 16/737,785

(22) Filed: Jan. 8, 2020

(65) Prior Publication Data

US 2020/0138614 A1    May 7, 2020

Related U.S. Application Data

(63) Continuation of application No. 15/669,650, filed on Aug. 4, 2017, now Pat. No. 10,561,511, which is a
(Continued)

(30) Foreign Application Priority Data

Apr. 7, 2009    (GB) ...................... 0906065

(51) Int. Cl.
*A61F 2/966*     (2013.01)
*A61F 2/958*     (2013.01)
(Continued)

(52) U.S. Cl.
CPC .............. *A61F 2/966* (2013.01); *A61F 2/856* (2013.01); *A61F 2/89* (2013.01); *A61F 2/958* (2013.01);
(Continued)

(58) Field of Classification Search
CPC .. A61F 2/95; A61F 2/962; A61F 2/966; A61F 2002/9522
See application file for complete search history.

(56) References Cited

U.S. PATENT DOCUMENTS 6,391,050 B1    5/2002  Broome
7,632,296 B2   12/2009  Malewicz
(Continued)

FOREIGN PATENT DOCUMENTS

WO    2006133959 A1   12/2006
WO    2008136329 A1   11/2008
(Continued)

OTHER PUBLICATIONS

PCT/EP2010/054592 filed Apr. 7, 2010 International Preliminary Report on Patentability dated Oct. 11, 2011.
(Continued)

*Primary Examiner* — Ashley L Fishback
(74) *Attorney, Agent, or Firm* — Rutan & Tucker LLP

(57) ABSTRACT

A method of making a delivery system for a prosthesis includes providing a catheter shaft, sliding a plurality of rings over the catheter shaft, each of the rings having an inner diameter larger than an outer diameter of the catheter shaft, fixing a pull wire to each of the plurality of rings at a common circumferential location of the catheter shaft, and coupling a sheath to the pull wire, the sheath positioned over the prosthesis at a distal end of the catheter shaft. Fixing the pull wire to each of the plurality of rings can include wrapping a heat shrink film around each of the plurality of rings and the pull wire, and heating the heat shrink material.

5 Claims, 1 Drawing Sheet

Related U.S. Application Data continuation of application No. 15/293,214, filed on Oct. 13, 2016, now Pat. No. 9,737,428, which is a continuation of application No. 14/822,797, filed on Aug. 10, 2015, now Pat. No. 9,492,299, which is a continuation of application No. 13/263,701, filed as application No. PCT/EP2010/054592 on Apr. 7, 2010, now Pat. No. 9,107,771.

(60) Provisional application No. 61/167,268, filed on Apr. 7, 2009.

(51) Int. Cl.
| | | |
|---|---|---|
| *A61F 2/856* | (2013.01) | |
| *A61F 2/89* | (2013.01) | |
| *A61F 2/01* | (2006.01) | |
| *A61F 2/95* | (2013.01) | |
| *A61F 2/82* | (2013.01) | |

(52) U.S. Cl.
CPC ............ *A61F 2/011* (2020.05); *A61F 2/9522* (2020.05); *A61F 2002/823* (2013.01); *A61F 2002/9665* (2013.01); *A61F 2220/0033* (2013.01)

(56) References Cited

U.S. PATENT DOCUMENTS

| | | |
|---|---|---|
| 7,780,693 B2 | 8/2010 | Brady et al. |
| 7,998,112 B2 | 8/2011 | Chow et al. |
| 9,107,771 B2 | 8/2015 | Wubbeling et al. |
| 9,492,299 B2 | 11/2016 | Wuebbeling et al. |
| 9,737,428 B2 | 8/2017 | Wuebbeling et al. |
| 9,750,625 B2 * | 9/2017 | Dorn ..................... A61F 2/962 |
| 10,561,511 B2 | 2/2020 | Wuebbeling et al. |
| 2003/0093106 A1 | 5/2003 | Brady et al. |
| 2005/0070844 A1 | 3/2005 | Chow et al. |
| 2006/0200221 A1 | 9/2006 | Malewicz |
| 2012/0083869 A1 | 4/2012 | Wubbeling et al. |
| 2017/0325981 A1 | 11/2017 | Wuebbeling et al. |

FOREIGN PATENT DOCUMENTS

| | | |
|---|---|---|
| WO | 2009011866 A1 | 1/2009 |
| WO | 2010115925 A1 | 10/2010 |

OTHER PUBLICATIONS

PCT/EP2010/054592 filed Apr. 7, 2010 International Search Report dated Jul. 21, 2010.
PCT/EP2010/054592 filed Apr. 7, 2010 Written Opinion dated Jul. 21, 2010.
U.S. Appl. No. 13/263,701, filed Dec. 19, 2011 Advisory Action dated Oct. 7, 2014.
U.S. Appl. No. 13/263,701, filed Dec. 19, 2011 Final Office Action dated Jul. 8, 2014.
U.S. Appl. No. 13/263,701, filed Dec. 19, 2011 Non-Final Office Action dated Dec. 19, 2013.
U.S. Appl. No. 13/263,701, filed Dec. 19, 2011 Non-Final Office Action dated Dec. 26, 2014.
U.S. Appl. No. 13/263,701, filed Dec. 19, 2011 Notice of Allowance dated Apr. 17, 2015.
U.S. Appl. No. 14/822,797, filed Aug. 10, 2015 Final Office Action dated Apr. 28, 2016.
U.S. Appl. No. 14/822,797, filed Aug. 10, 2015 Non-Final Office Action dated Oct. 28, 2015.
U.S. Appl. No. 14/822,797, filed Aug. 10, 2015 Notice of Allowance dated Jul. 15, 2016.
U.S. Appl. No. 15/293,214, filed Oct. 13, 2016 Non-Final Office Action dated Dec. 23, 2016.
U.S. Appl. No. 15/293,214, filed Oct. 13, 2016 Notice of Allowance dated Apr. 18, 2017.
U.S. Appl. No. 15/669,650, filed Aug. 4, 2017 Non-Final Office Action dated Jun. 17, 2019.
U.S. Appl. No. 15/669,650, filed Aug. 4, 2017 Notice of Allowance dated Sep. 27, 2019.

* cited by examiner

DELIVERY SYSTEM FOR A PROSTHESIS

PRIORITY

This application is a continuation of U.S. patent application Ser. No. 15/669,650, filed Aug. 4, 2017, now U.S. Pat. No. 10,561,511, which is a continuation of U.S. patent application Ser. No. 15/293,214, filed Oct. 13, 2016, now U.S. Pat. No. 9,737,428, which is a continuation of U.S. patent application Ser. No. 14/822,797, filed Aug. 10, 2015, now U.S. Pat. No. 9,492,299, which is a continuation of U.S. patent application Ser. No. 13/263,701, filed Dec. 19, 2011, now U.S. Pat. No. 9,107,771, which is a U.S. national stage application under 35 U.S.C. § 371 of International Application No. PCT/EP2010/054592, filed Apr. 7, 2010, claiming priority to United Kingdom Patent Application No. 0906065.8, filed Apr. 7, 2009, and to U.S. Provisional Application No. 61/167,268, filed Apr. 7, 2009, each of which is incorporated by reference in its entirety into this application.

TECHNICAL FIELD

This invention relates to a delivery system for a prosthesis such as a self-expanding stent, the deli very system taking the form of a catheter that includes a sheath surrounding the stent, and a pull wire to pull the sheath proximally, progressively to release the stent.

BACKGROUND

The published literature includes a multitude of designs for stent delivery catheters, which will deploy a self-expanding stent, such as one made out of nickel titanium shape memory alloy, at a site of stenting within the human body. For deployment, a sheath that surrounds the stent and confines it radially is pulled proximally, relative to the stent, by a so called "pull wire". Such a pull wire invariably lies within a lumen running lengthwise along the shaft of the catheter, all the way back to a hand unit at the proximal end of the catheter, where it can be pulled, to pull back the sheath. Typically, there is an annular member at the proximal end of the sheath, that is slidable on the catheter shaft, and which is fixed in relation to the proximal end of the sheath and the distal end of the pull wire. Pulling on the pull wire pulls the annular component proximally on the catheter shaft and this in turn pulls the sheath proximally relative to the stent that lies around the shaft, distal of the annular element.

It is well known that the act of putting tension on the sheath that surrounds a self-expanding stent, in order progressively to deploy the stent, can have the effect of pulling the stent proximally. Unless this tendency is controlled and restricted, if not prevented, then there is a risk that the stent will be pulled proximally relative to the location in the bodily lumen where it is to be deployed. Obviously, deployment proximal of the intended deployment location is undesirable. There have been various proposals about how to minimise the extent of such proximal movement of the stent. One proposal, see Applicant's WO 2003/003944, is to establish within the catheter shaft a continuous strand of metal that runs all the way from the hand unit to a pusher ring that abuts the stent and so can resist proximal movement of the stent, when the sheath around the stent is pulled back proximally. However, the present inventors have determined that, even with a continuous metal strand resisting proximal movement of the stent, there is still a residual possibility that the stent will end up being placed at a location proximal of the desired location, and it is one object of the present invention to further minimise the chances of this adverse event occurring.

SUMMARY OF THE INVENTION

The present invention provides a delivery system for a prosthesis, as categorised above, the system including at least one fixation element having a proximal end and a distal end and being disposed within a flexible portion of the length of the catheter shaft that lies between the proximal end of the prosthesis-confining sheath and the proximal end of the catheter shaft, the fixation element serving to limit a radial distance between the axis of the pull element outside the shaft, that pulls back the sheath, and the axis of the catheter shaft along the length of the fixation element.

Important to note is that, with the invention, the pull element (the archetype is a pull wire) lies outside the specified flexible portion of the length of the catheter shaft.

A necessary property of the catheter shaft is pushability, to push the distal end of the catheter into the location where the prosthesis is to be deployed, and to resist proximal movement of the prosthesis, when the confining sheath is pulled back proximally. A shaft in the form of a tube with a lumen is likely to be advantageous. The lumen can be used for advancing the delivery system over a guidewire, and for flushing the distal end structure of the delivery system, and for delivery of contrast fluids. In the delivery systems hitherto, the pull element has been disposed within a lumen of the catheter shaft, but the present inventors have realised that disposing the pull element in this way can increase unnecessarily the complexity of construction, and the passing diameter, of the delivery system. By placing the pull element outside the catheter shaft, a degree of simplification is achievable, with an improvement in the transfer of tensile stresses from the hand unit to the sheath surrounding the self-expanding prosthesis.

What the present inventors have realised, however, is that locating the pull wire outside the catheter shaft can set up the conditions for bowing of the catheter shaft, with the shaft as the "bow" and the pull wire as the "bow string". Evidently, the greater the degree of bowing, the shorter is the straight line distance between the two ends of the bow. With the delivery system of the invention, the opposite ends of the bow are represented by the hand unit and the distal end of the catheter containing the stent. When the catheter shaft is within a bodily lumen and there is scope for the line of the catheter shaft and the line of the pull wire to become spaced apart from each other, there is the possibility for the stent to move proximally, prior to deployment.

With this realisation, the present inventors have applied their minds to ways of mitigating this problem. The present invention emerges from these reflections.

The invention is defined in claim 1 below. The dependent claims are directed to optional features and preferred embodiments.

The "pusher element" in the delivery system of the invention is any element that restrains the prosthesis from being pulled proximally by the tension in the pull element. Typically, it takes the form of an annular ring that abuts the proximal end of the prosthesis, but a multitude of other possibilities exist, as the patent literature reveals. There are, for example, cushions which conform to a contoured luminal surface of a self-expanding stent, and various detent devices which can engage with one surface feature or another of the prosthesis to be delivered.

The archetypal fixation element according to the present invention is a simple loop of heat shrink material that circumscribes both the pull wire and the catheter shaft. Other materials will serve, but heat shrink material is attractive because it keeps the overall passing diameter of the catheter shaft system to a minimum, with the pull wire drawn down tight on the abluminal surface of the catheter shaft. The heat shrink material does not slide axially on the abluminal surface of the catheter shaft, but the pull wire can slide relative to its point of contact with the abluminal surface of the catheter shaft, and relative to its arc of contact with the heat shrink material that wraps around it.

Such bands of heat shrink material can be placed at spaced intervals along the shaft of the catheter, at a pitch that will be appropriate to the application for which the delivery system is needed. A delivery procedure that is going to involve high magnitude tensile forces, in a particularly tortuous bodily lumen, might indicate a closer spacing of fixation elements than a procedure which occurs with milder tension forces in a less tortuous lumen.

An alternative form of fixation element is contemplated, one that is slidable on the catheter shaft, but slides with movement of the pull wire. One can imagine the pull wire moving relative to the catheter shaft, with the rings of the fixation elements sliding along the shaft, as curtain rings do with a curtain being drawn along a curtain rail. The additional frictional resistance to proximal movement of the pull element relative to the catheter shaft caused by such rings ought to be minimal, even with a relatively large number of rings to keep all portions of the length of the pull wire close to the abluminal surface of the catheter shaft. In one embodiment, each such fixation element ring is freely slidable on the abluminal surface of the catheter shaft, with a film of heat shrink material being wrapped around the sliding ring and the pull wire, so as to draw the pull wire down tight on the abluminal surface of the sliding ring.

This is not to say that sliding movement of the pull wire relative to the sliding ring is impossible. For safety reasons, it is highly desirable that there should be some capability for the pull wire to slide relative to the ring surrounding the catheter shaft, just in case that ring is somehow blocked from further sliding along the catheter shaft. If this were to happen partway through stent deployment, so that the pull wire could not be pulled further proximally, so that the proximal portion of the stent could not be released from its confining sheath, the results would be most unfortunate for the patient. Thus, it ought to be possible for the pull wire to be further withdrawn, even if further proximal movement of a fixation element ring is somehow prevented.

In a catheter delivery system for a self-expanding stent confined inside a sheath at the distal end of the catheter shaft, it is common for the sub-assembly of stent and sheath to be freely rotatable on the shaft. In such cases, a pull wire that runs outside the shaft could end up wound helically around the shaft, if the sheath rotates on the shaft during advancement of the distal end of the catheter, from the point of entry to the bodily lumen until it arrives at the stenting location.

Any such winding can adversely affect (or even eliminate) the capability of the pull wire to pull the sheath proximally to release the stent.

The fixation element of the present invention can in such circumstances perform a valuable additional function, namely, to reduce the amount of any such winding of the pull wire around the shaft, and mitigate the adverse effects of any winding, should it nevertheless occur.

Another situation in which sliding of the pull wire through the sliding ring is needed is when the sliding rings are spaced apart by distances that are smaller than the length the pull wire has to be pulled back. In such a case, by the end of the pulling back, the hitherto spaced rings will be shunted up into an abutting, stacked configuration at the proximal end of the shaft on which they slide. The most relative movement between ring and wire will have been with the most proximal of the stack of rings.

For a better understanding of the present invention, and to see more clearly how the same may be carried into effect, reference will now be made, by way of example, to the accompanying drawings.

DETAILED DESCRIPTION

Figure 1:
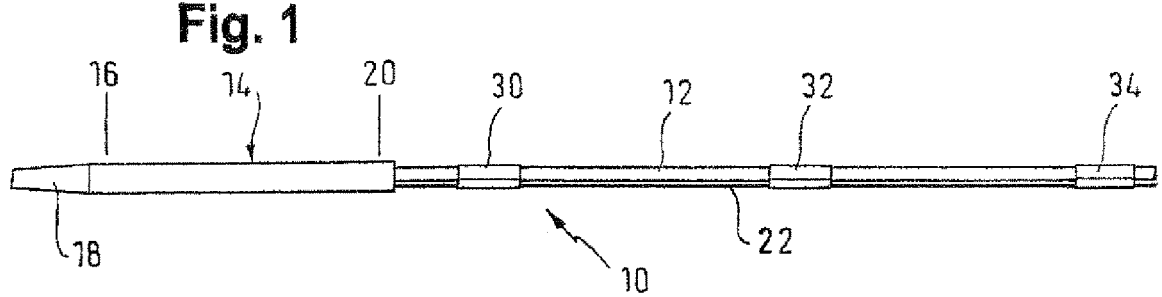
FIG. 1 is a view from the side of the distal end of a catheter which is a delivery system for a self-expanding stent.

Looking first at FIG. 1, many of the components of the system will be familiar to those skilled in the art. The delivery system 10 of which the distal part is shown in FIG. 1 is based on a tube 12 which constitutes a catheter shaft. That tube carries at its distal end 14 a sheath 16 with a tapered tip 18 and a proximal end 20 within which lies (not visible in FIG. 1) an annulus to which is welded a pull wire 22. When the stent inside the sleeve 1 6 is to be deployed, tension is put on the pull wire 22 and this tension is passed through to the sheath 16 via the annulus within the proximal end 20 of the sheath. The sheath is pulled proximally, until its distal end 18 is proximal of the proximal end of the stent within the sheath 16, at which point the stent is fully deployed and the delivery system can be withdrawn proximally out of the bodily lumen.

In FIG. 1, the catheter shaft is shown rigorously straight. However, in a typical placement within the human body, the shaft 12 will lie along a bodily lumen that is not straight. When tension is placed on the pull wire 22, that pull wire will likely migrate to the inside of the bend, along the bodily lumen, with the catheter shaft (in endwise compression) bowing outwardly to the outside of each bend of the tortuous lumen. To prevent the excessive opening up of a spacing between the shaft 12 and the pull wire 22, the pull wire 22 carries fixation elements, of which three are shown in FIG. 1. These fixation elements 30, 32 and 34 lie at spaced intervals along the length of the pull wire 22 and include a lumen that receives the catheter shaft 12. When the pull wire 22 moves proximally relative to the shaft 12, the fixation elements 30, 32 and 34 move with the pull wire, all proximally relative to the shaft 12, and at first stay at the same distance from the proximal end 20 of the sheath 14. With the intervals between any two fixation elements being relatively small, there is a correspondingly much reduced scope for a gap to open up, between the path of the catheter shaft 12 and the line of the pull wire 22, however tortuous the bodily lumen within which the catheter shaft lies, and however compliant is the tissue at the inside and the outside of the bend in the lumen where the pull wire 22 and shaft 12 tend to migrate.

As each ring arrives with the pull wire at the proximal end of its range of free movement on the catheter shaft, it ceases to slide any further proximally and, from then on, the pull wire slides through that ring till the pulling process is complete.

Figure 2:
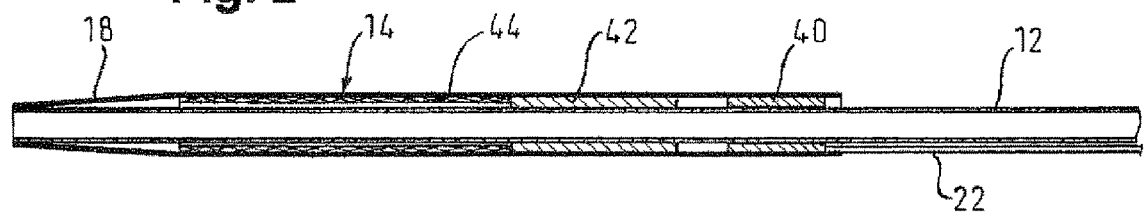
FIG. 2 is a longitudinal axial section through the distal end portion of the system shown partially in FIG. 1.

Turning to FIG. 2, the section allows us to see the annulus 40 at the proximal end of the sleeve 14, by means of which the pull wire 22 can pull back the sheath proximally. We can also see the path of the catheter shaft 12, coaxial with the sheath 14, all the way to the distal end of the tapered tip 18 of the sheath. The shaft carries a pusher ring 42 that abuts the proximal end of a stent 44 that is to be deployed by a proximal withdrawal of the sheath 14. The catheter shaft 12 has a lumen (not visible) which receives a guidewire (not shown) along which the catheter delivery system is advanced to the site of stenting.

Figure 3:
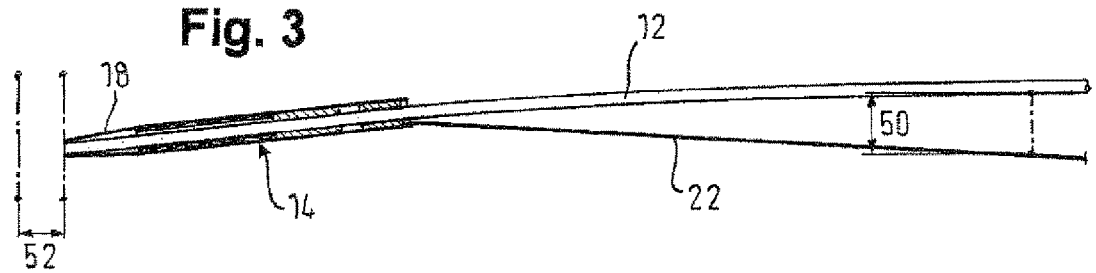
FIG. 3 is a view from the side of the distal end of the delivery system shown in FIG. 1, absent the fixation elements of FIG. 1 and with the pull wire under tension.

Turning to FIG. 3, this drawing is simply to make the point that the opening up of a gap 50 between the pull wire 22 and the catheter shaft 12 has consequences for the position of the distal tip 1 8 of the delivery system As the drawing shows, a gap such as 50 corresponds to a retreat proximally of the distal tip 18 of the delivery system, by an amount represented here schematically by reference 52. Any such proximal retreat is unwanted, and prejudicial to perfect placement of the stent at the intended site of stenting. The fixation elements of the invention act to minimise any such proximal retreat 52.

Figure 4:
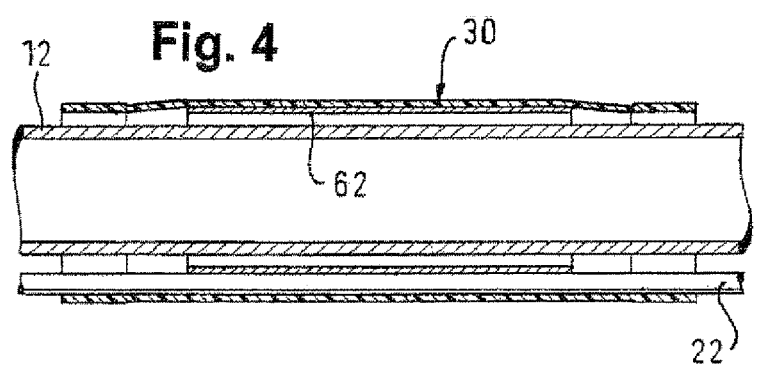
FIG. 4 is a section through that part of the system of FIG. 1 that includes a fixation element.
Figure 5:
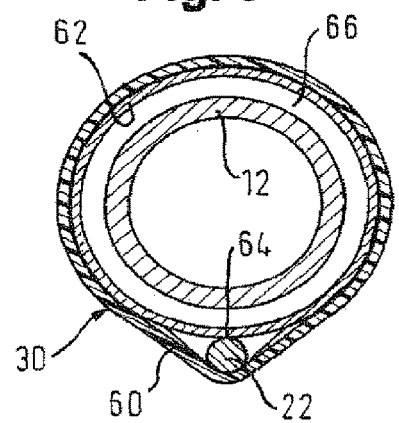
FIG. 5 is a transverse section through the fixation element of FIG. 4.

FIGS. 4 and 5 are orthogonal sections through a fixation element such as the element 30. The pull wire 22 lies within an arc of a tube 60 of shrink film material that presses on an arc of the pull wire 22 and urges it towards a slider ring 62. Depending on the compliance of the material from which the slider ring 62 is formed, the point of contact 64 of the pull wire on the abluminal surface of the slider ring 62 will be an arc of greater or lesser length. The length of that arc will likely affect the magnitude of the frictional forces that would restrain the pull wire 22 from moving longitudinally relative to the fixation element. As mentioned above, for safety reasons it is desirable that these frictional forces can be overcome, whenever that is imperative, so the friction operating between the pull wire 22, the shrink film 60 and the slider ring 62 should not be more than a predetermined design maximum.

Conversely, the amount of friction between the slider ring 62 and the catheter shaft 12 can be minimised and should be reduced to a level a s low as is consistent with all other design factors. For example, when the objective is to keep to a minimum the passing diameter of the shaft of the delivery system, one would wish the annular gap 66 between the luminal surface of the slider ring 62 and the abluminal surface of the catheter shaft 12 to be minimised. However, when the gap 66 becomes excessively small, one can anticipate that the forces of friction between the slider ring 62 and the catheter shaft 12 might increase, even to levels that prejudice easy pulling back of the sheath 1 4 from the stent 44, using the pull wire 22. As a general rule, the greater the number of rings, and the greater the axial length of each one, the greater will be the aggregate drag they impose on the pull wire and so, consequentially, the greater the need for an annular gap between the rings and the shaft. Since the rings nearest the distal end of the shaft will slide the furthest, proximally along the shaft, one should aim to ensure that the drag they impose on the pull wire is as small as possible.

Selection of materials for catheters for delivering stents is a technical field all of itself, but a field which is familiar for skilled readers of the present application. Accordingly, readers are here spared a tour of that technical field.

Although the illustrated embodiment includes a sheath with a tapered distal tip 18, readers will well know that it is more typical of pull wire delivery systems to find a sheath with a cylindrical distal end, but a tapered distal tip on the distal end of the inner catheter shaft, distal of the sheath. Such architecture is of course within the scope of the inventive concept set out in this application.

Although the invention is seen as being primarily useful for self-expanding stents, it may be useful also for stents that are not self-expanding or, indeed, for other categories of prosthesis, besides stent and stent grafts. For example, the invention may useful for systems to deliver filter elements for placement in the arterio-vascular system.

In general, the invention will find application whenever a pull wire is part of a catheter device.

What is claimed is:

1. A method of making a delivery system for a prosthesis, comprising:
   providing a catheter shaft;
   sliding a plurality of rings over the catheter shaft, each of the plurality of rings having an inner diameter larger than an outer diameter of the catheter shaft;
   fixing a pull wire to each of the plurality of rings at a common circumferential location of the catheter shaft; and
   coupling a sheath to the pull wire, the sheath positioned over the prosthesis at a distal end of the catheter shaft.

2. The method of making according to claim 1, wherein the plurality of rings comprises a first ring, a second ring, and a third ring spaced apart along the catheter shaft proximal of a proximal end of the sheath.

3. The method of making according to claim 1, wherein fixing the pull wire comprises wrapping a heat shrink film around each of the plurality of rings and the pull wire, and heating the heat shrink material.

4. The method of making according to claim 3, wherein wrapping the heat shrink film creates a first frictional force on the pull wire with respect to the plurality of rings, the first frictional force being less than a predetermined design maximum to permit movement of the pull wire with respect to the plurality of rings.

5. The method of making according to claim 4, wherein the first frictional force is greater than a frictional force between each of the plurality of rings and the catheter shaft to permit the plurality of rings to move proximally along the catheter shaft during removal of the sheath from the prosthesis.

* * * * *